United States Patent [19]
Negishi et al.

[11] Patent Number: 5,804,170
[45] Date of Patent: Sep. 8, 1998

[54] DEODORANT COMPOSITION

[75] Inventors: Osamu Negishi, Saitama; Tetsuo Ozawa, Ibaraki, both of Japan

[73] Assignee: Takasago Koryo Kogyo Kabushiki Kaisha (Takasago International Corporation), Tokyo, Japan

[21] Appl. No.: 681,913

[22] Filed: Jul. 30, 1996

[30] Foreign Application Priority Data

Jul. 31, 1995 [JP] Japan .................................. 7-212999

[51] Int. Cl.⁶ ........................... A61K 7/32; A61K 35/78; A61K 7/00
[52] U.S. Cl. ...................... 424/65; 424/195.1; 424/400; 424/401
[58] Field of Search .............................. 424/65, 400, 401, 424/195.1

[56] References Cited

U.S. PATENT DOCUMENTS

| | | | |
|---|---|---|---|
| 3,988,318 | 10/1976 | Copes et al. | 424/65 X |
| 3,988,351 | 10/1976 | Copes et al. | 548/519 |
| 4,708,809 | 11/1987 | Davis | 508/295 |
| 4,724,091 | 2/1988 | Davis | 508/412 |

Primary Examiner—Shelley A. Dodson
Attorney, Agent, or Firm—Sughrue, Mion, Zinn, Macpeak & Seas, PLLC

[57] ABSTRACT

A deodorant composition comprising a phenolic compound and an enzyme oxidizing said phenolic compound is disclosed. The deodorant composition is useful to remove environmental smells such as bad breath, the smell in refrigerator, smells derived from pets and domestic animals, smells in factories, the stench of factory effluent, and other smells that are offensive to people.

17 Claims, No Drawings

DEODORANT COMPOSITION

BACKGROUND OF THE INVENTION

1. Field of the Invention

The present invention relates to a deodorant composition, more particularly, a deodorant composition to remove environmental smells such as bad breath, the smell in refrigerator, smells derived from pets and domestic animals, smells in factories, the stench of factory effluent, and other smells that are offensive to people.

2. Description of the Related Arts

There are several kinds of smells surrounding us, for example, smells in refrigerators or the like, bad breath, smells of domestic animals, and so forth. Since these smells are offensive to people, various means for deodorization have been developed. One of well-known means is to remove the source substances of the stenches using an adsorbent. Well-known examples of such adsorbents are active carbon and teas containing catechins.

However, active carbon can neither adsorb a trace of substance nor be used for foods or other products which should be kept in one's mouth. Besides, active carbon has a further drawback that discarding the active carbon which have absorbed a great deal causes a deterioration of the earth environment. Meanwhile, natural substances like catechins are friendly to the earth environment and capable of blended with a chewing gum or the like to prevent bad smell. However, such substances are not sufficient in the deodorizing effect.

OBJECT OF THE INVENTION

Accordingly, an object of the present invention is to provide a deodorant composition which has an excellent deodorizing effect and is friendly to the earth environment.

SUMMARY OF THE INVENTION

The inventors earnestly investigated in view of the fact that phenolic compounds like catechins have deodorizing effects, and unexpectedly found that surprising deodorizing effects can be obtained when these compounds are used together with polyphenol oxidases, and finally, have achieved the present invention.

The deodorizing activities of the phenolic compounds are supposed to be exhibited by the following mechanism: the compounds are oxidized with oxygen or oxidases surrounding them to have highly reactive quinone structure; and the oxidized compounds react with substances causing stenches. In the present invention, polyphenol oxidases are intentionally made to coexist with the compounds. According to the present invention, it is expected the auto-oxidation would be promoted and that the stenches can be removed in a short time and at a high deodorizing rate.

In summary, an aspect of the present invention is a deodorant composition comprising at least one phenolic compound and at least oxidase capable of oxidizing said phenolic compounds.

DETAILED DESCRIPTION OF THE INVENTION

The phenolic compounds, which are one ingredient of the deodorant composition according to the present invention, include compounds having one or more of phenolic hydroxyl groups. The term "phenolic hydroxyl group" used herein stands for a hydroxyl group directly bonded to an aromatic ring like the benzene ring. The aromatic ring may be any of benzene, pyridine, thiophene, naphthalene, biphenyl, and other aromatic rings which have a structure to be converted into ketones by oxidation of hydroxyl groups. Benzene ring is most preferred.

The examples of the phenolic compounds may include diphenols such as catechol, 4-methylcatechol, 5-methylcatechol, resorcinol, 2-methylresorcinol, 5-methylresorcinol, and hydroquinone; biphenyldiols such as 4,4'-biphenyldiol and 3,4'-biphenyldiol; catechins such as (+)-catechin, (−)-epicatechin, (−)-epigallocatechin, (−)-epigallocatechin gallate; and catechol derivatives such as dopa, dopamine, chlorogenic acid, caffeic acid, paracoumaric acid, tyrosine. Preferable are catechol, catechins, tyrosine and chlorogenic acid, and particularly preferable are catechins and chlorogenic acid.

Two or more of the above-described compounds may also be used together in the present invention.

The enzymes capable of oxidizing the phenolic compounds, which are the other ingredient of the deodorant composition according to the present invention, include the following types of enzymes: enzymes which has a function of oxidizing the above-described phenolic compounds into compounds having the quinone structure; and oxidases of the same kind which has a further function of adding phenolic hydroxyl groups and oxidizing the resultants into quinones. The oxidases to be used are not limited as long as they have the above-described function. The examples of such oxidases may include polyphenol oxidases, monophenol oxidases, oxidases forming hydrogen peroxide, and peroxidases. More specifically, preferable are laccases, tyrosinases, glucose oxidases, and peroxidases. The above-described oxidases may also be used in combination thereof.

Further, substances or compositions that contain any of the above-described enzymes should fall within the scope of the enzyme according to the present invention which can oxidize the phenolic compounds. The example of such substances or compositions are extracts of plants or microorganisms containing the above-described enzymes, and powders such as acetone powders, prepared from the plants or the microorganisms. Preferred plants containing the above-oxidases are fruits and vegetables such as apples, pears, peaches, plums, apricots, cherries, burdocks, potatoes, eggplants and chicory. Also preferred microorganisms are fungi classified under genus Agricus or the genus Boletus such as *A. bisporus, B. pulverulentus* and *B. subvelutipes.*

While enzymes commercially available can be used for the present invention, they can also be prepared by any suitable method publicly known before the filing date of the present application.

In addition to the above-described two ingredients, carrier materials, stabilizers, bulking agents and other conventional additives may optionally be added or blended.

The deodorant composition according to the present invention can quench stinking substances, for example, sulfur-containing compound such as mercaptan, and nitrogen-containing compound such as indole, skatole, and amines.

The deodorization using the deodorant composition of the present invention is achieved by subjecting the composition to contact reaction in the presence of the stinking substances. For easy progression of the reaction, it is desirable to mix the composition and the stinking substances. On mixing, presence of water is advantageous since the reaction progresses smoothly.

Though the temperature for the deodorization is not limited as long as it is set within a temperature range where the enzymatic reaction progresses, the ambient temperature is suitable to mixing because the reaction quickly progresses. The reaction time from a few minute to some ten hours are usually enough for the deodorization, though it depends on the types of the enzymes and amount of the composition used.

Other reaction conditions can be optionally set without any limitation, provided that the oxidation reaction progresses in the conditions.

The present invention will be further illustrated with the following examples, which are not directed to limiting the scope of the present invention.

REFERENTIAL EXAMPLE 1

The below-described method is a preparation method for producing an enzyme capable of oxidizing phenolic compounds, namely, the preparation method for producing an acetone powder.

Four hundreds milliliters of acetone at −20° C. was added to 100 g of a plant or a fungus (such as apples or burdocks as described in below Examples), and the mixture was subjected to homogenization with a mixer followed by aspiration filtration. The residue was sufficiently washed with 500 ml of 80% acetone solution at 5° C. After removal of acetone, the residue was freeze-dried to obtain an acetone powder.

Examples 1–7

A commercially available enzyme (manufactured by SIGMA Chemical Co.) described in Table 1 was placed into a 30-ml vial at an amount described in Table 1 with 1 ml of water and 2 $\mu$l of 15% $CH_3SNa$ aqueous solution as a stinking substance. Then, 0.5 ml of an aqueous solution containing 2 mg of a commercially available substrate (a phenolic compound) described in Table 1. was added and the mixture was shaken with hands. The color of the reaction mixture changed by the shaking or standing for the time described in Table 1. Ten milliliters of the gas in the vial was then applied to a detector tube (manufactured by Gastec Co., Ltd.) to measure the concentration of the stinking substance which had remained in the gas. The results are shown in Table 1.

TABLE 1

| Sample No. | Enzyme | Amount of Addition (mg) | Substrate | Reaction Time | Reading of Detector tube | Rate of Deodorization (%) |
| --- | --- | --- | --- | --- | --- | --- |
| Example 1 | Tyrosinase[1] | 1 | Catechol | 10 min. or less | 0 | 100 |
| Example 2 | Tyrosinase | 1 | (−)-Epi-catechin | 3 hrs. | 0 | 100 |
| Example 3 | Tyrosinase | 1 | Chlorogenic acid | 4.5 hrs. | 0 | 100 |
| Example 4 | Tyrosinase | 1 | Tyrosine | 2 hrs. | 0 | 100 |
| Example 5 | Tyrosinase | 1 | Dopa | 1.5 hrs. | 0 | 100 |
| Example 6 | Peroxidase[2] | 0.4 | Catechol | 1.5 hrs. | 0 | 100 |
| Example 7 | Glucose oxidase[3] and Peroxidase | 0.2 0.04 | Glucose and Chlorogenic acid | 10 min. or less | 0 | 100 |
| Comparative 1 | — | — | Chlorogenic acid | 4.5 hrs. | 48 | 0 |

Note: Product number of the Enzyme; [1]: T-7755, [2]: P-8125, [3]: G-6125
: Reading of detector tube is the value of the scale of the detector tube at the boundary of the color change.

Examples 8–14

Ten milligrams of the above-prepared acetone powder and 1 ml of water were placed in a 30-ml vial to make a suspension. Then, 2 $\mu$l of 15% $CH_3SNa$ aqueous solution was added to the suspension. Further, 0.5 ml of an aqueous solution containing 2 mg of a commercially available substrate (a phenolic compound) described in Table 2 was added and the mixture was shaken with hands for 10 min. Ten milliliters of the gas in the vial was then applied to a detector tube (manufactured by Gastec Co., Ltd.) to measure the concentration of the stinking substance which had remained in the gas. Further the gas was smelled for a sensory examination. The results are shown in Table 2.

TABLE 2

| Sample No. | Material of Enzyme (Acetone Powder) | Substrate | Reading of Detector Tube | Rate of Deodorization | Sensory Examination |
|---|---|---|---|---|---|
| Comparative 2 | — | — | 45 | 0 | Stinking |
| Comparative 3 | Apple | — | 50 | 0 | Stinking |
| Comparative 4 | — | Chlorogenic acid | 47 | 0 | Stinking |
| Example 8 | Apple | Chlorogenic acid | 0 | 100 | No stinking |
| Example 9 | Burdock | Chlorogenic acid | 0 | 100 | No stinking |
| Comparative 5 | — | (−)-Epi-catechin | 47 | 0 | Stinking |
| Example 10 | Pear | (−)-Epi-catechin | 0 | 100 | No stinking |
| Example 11 | Burdock | (−)-Epi-catechin | 0 | 100 | No stinking |
| Comparative 6 | — | Instant Coffee | 53 | 0 | Stinking |
| Example 12 | Burdock | Instant Coffee | 0 | 100 | No stinking |
| Example 13 | Pear | Instant Coffee | 25 | 52.8 | Slightly stinking |
| Example 14 | Mushroom[*4] (A. bisporus) | Catechol | 0 | 100 | No stinking |

Note: [*4]; The amount of the acetone powder was 40 mg.

Example 15

Three grams of a chewing gum (A) was prepared so as to contain 2 mg of chlorogenic acid and 10 mg of burdock acetone powder. For comparison, three grams of another chewing gum (B) was also prepared so as to contain 2 mg of chlorogenic acid.

Subjects (A) were forced to keep 0.5 g of grated garlic in their mouths for 5 min. to be rendered stinking, and rinsed their mouths with water. After the subjects (A) chewed the above-mentioned chewing gum (A) for 10 min., the halituses were collected individually in polyester bags and examined on the smells. The same procedure was carried out in subjects (B), except that they chewed the chewing gum (B) instead of the chewing gum (A). As a result, the each breath of the subjects (A) stank little while that of the subjects (B) still remains stinking of garlic.

Example 16

There were prepared 0.5 ml of an aqueous solution containing 2 mg of chlorogenic acid and 40 mg of burdock acetone powder. For comparison, there was prepared another 0.5 ml of the aqueous solution containing 2 mg of chlorogenic acid.

Subjects (C) were forced to keep 0.5 g of grated garlic in their mouths for 5 min. to be rendered stinking, and rinsed their mouths with water. The subjects (C) were then made to keep the above-mentioned 0.5 ml of the aqueous solution containing 2 mg of chlorogenic acid and the 40 mg of burdock acetone powder in their mouths for 5 min. After rinsing their mouths, the halituses of the subjects (C) were collected individually in the same manner described in Example 15, and examined on the smells. The same procedure was carried out in subjects (D), except that they were made to keep 0.5 ml of the aqueous solution containing 2 mg of chlorogenic acid alone in their mouths instead of the combination of the solution and the burdock acetone powder. As a result, the each breath of the subjects (C) stank little while that of the subjects (D) still remains stinking of garlic.

Example 17

Ten milligrams of an apple acetone powder was placed in a 30-ml vial with 1 ml of water and 20 μl of a fluid separated from excrement of domestic animals. Zero point five milliliters of an aqueous solution containing 2 mg of chlorogenic acid was further added to the mixture and shaken with hands for 10 min. The gas in the vial was then smelled for the sensory examination. For comparison, three mixtures were prepared. They had the same composition as the above-prepared mixture, except that one of them lacked 10 mg of the apple acetone powder, another of them lacked 0.5 ml of the aqueous solution containing 2 mg of chlorogenic acid, and the remaining of them lacked both the acetone powder and the solution chlorogenic acid. The mixtures were then treated in the same manner as the above, and gases derived from them were also smelled for the sensory examination. The results are shown in Table 3.

TABLE 3

| Sample No. | Chlorogenic acid | Acetone Powder | Sensory Examination |
|---|---|---|---|
| Comparative 7 | None | None | Strong stench of amine and Stench of excrement existed. |
| Comparative 8 | Present | None | The stench of amine disappeared, while strong stench of mercaptan still remained. |
| Comparative 9 | None | Present | The stench of amine disappeared, while strong stench of mercaptan still remained. |
| Example 17 | Present | Present | Stenches disappeared. |

Advantages of the Invention

In the deodorization method using the deodorant composition according to the present invention, a phenolic compound as the deodorant base material is activated by coexisting with an enzyme capable of oxidizing the compound, and by virtue of that, the oxidization reaction progresses in short time and an excellent deodorization effect can be obtained. The deodorant composition according to the present invention would have high safety by use of food materials such as vegetables and fungi as an ingredient, and therefore, can be used for prevention of bad breath. Further, the deodorant composition of the present invention can also be used for removal of environmental stenches without causing problems such as environmental contamination.

We claim:

1. A composition comprising a phenolic compound and an enzyme capable of oxidizing said phenolic compound wherein said composition has a deodorizing effect.

2. A composition comprising a phenolic compound and an acetone powder containing an enzyme capable of oxidizing said phenolic compound wherein said composition has a deodorizing effect.

3. A composition as claimed in claim 2, wherein said acetone powder is prepared from a plant or a microorganisms.

4. A composition as claimed in claim 3, wherein said plant is a fruit or vegetable.

5. A composition as claimed in claim 3, wherein said microorganism is a fungus.

6. A composition as claimed in claim 1, wherein said phenolic compound comprises an aromatic ring having at least one hydroxyl group which is converted into a ketone group by oxidation in the presence of an enzyme capable of oxidizing said phenolic compound.

7. A composition as claimed in claim 1, wherein said phenolic compound is selected from the group consisting of a catechol, a biphenyldiol, a catechin, and mixtures thereof.

8. A composition as claimed in claim 7, wherein said catechol is selected from the group consisting of 4-methylcatechol, 5-methylcatechol, resorcinol, 2-methylresorcinol, 5-methylresorcinol, hydroquinone and mixtures thereof.

9. A composition as claimed in claim 7, wherein said biphenyldiol is selected from the group consisting of 4,4'-biphenyldiol, 3,4'-biphenyldiol and mixtures thereof.

10. A composition as claimed in claim 7, wherein said catechin is selected from the group consisting of (+)-catechin, (−)-epicatechin, (−)-epigallocatechin, (−)-epigallocatechin gallate and mixtures thereof.

11. A composition as claimed in claim 7, wherein said catechol derivative is selected from the group consisting of dope, dopamine, chlorogenic acid, caffeic acid, paracoumaric acid, tyrosine and mixtures thereof.

12. A composition as claimed in claim 7, wherein said phenolic compound is selected from the group consisting of catechin, chlorogenic acid and mixtures thereof.

13. A composition as claimed in claim 1, wherein said enzyme is selected from the group consisting of a polyphenol oxidase, a monophenol oxidase, an oxidase forming hydrogen peroxide, a peroxidase and mixtures thereof.

14. A composition as claimed in claim 1, wherein said enzyme is selected from the group consisting of laccase, tyrosinase, glucose oxidase, peroxidase and mixtures thereof.

15. A composition as claimed in claim 4, wherein said fruit or vegetable is selected from the group consisting of apple, pear, peach, plum, apricot, cherry, burdock, potato, eggplant, and chicory.

16. A composition as claimed in claim 5, wherein said fungus is at least one selected from the group consisting of the genus Agricus and the genus Boletus.

17. A composition as claimed in claim 5, wherein said fungus is at least one selected from the group consisting of *A. bisporus, B. pulverulentus* and *B. subvelutipes.*

* * * * *